US006627111B2

(12) United States Patent
Swanson et al.

(10) Patent No.: US 6,627,111 B2
(45) Date of Patent: Sep. 30, 2003

(54) ORGANIC LIGHT EMITTING DISPLAYS AND NEW FLUORESCENT COMPOUNDS

(75) Inventors: Sally Ann Swanson, San Jose, CA (US); Gregory Michael Wallraff, Morgan Hill, CA (US)

(73) Assignee: International Business Machines Corp., Armonk, NY (US)

( * ) Notice: Subject to any disclaimer, the term of this patent is extended or adjusted under 35 U.S.C. 154(b) by 86 days.

(21) Appl. No.: 09/798,894

(22) Filed: Mar. 6, 2001

(65) Prior Publication Data

US 2002/0127428 A1 Sep. 12, 2002

(51) Int. Cl.$^7$ ..................... C09K 11/06; C07D 407/04; H05B 33/14
(52) U.S. Cl. ........................ 252/301.16; 252/301.35; 428/690; 428/917; 313/504; 549/283; 549/288; 548/305.1
(58) Field of Search ................. 428/690, 917; 313/504, 506; 257/40, 102, 103; 252/301.16, 301.35, 301.22, 301.32; 549/283, 288, 399, 404, 426; 544/99; 548/305.1

(56) References Cited

U.S. PATENT DOCUMENTS

| | | | |
|---|---|---|---|
| 5,126,214 A | 6/1992 | Tokailin et al. ............. | 428/690 |
| 5,281,489 A * | 1/1994 | Mori et al. .................. | 428/690 |
| 5,294,870 A | 3/1994 | Tang et al. ................. | 313/504 |
| 5,705,285 A | 1/1998 | Shi et al. .................... | 428/690 |
| 6,020,078 A | 2/2000 | Chen et al. ................. | 428/690 |
| 6,268,072 B1 * | 7/2001 | Zheng et al. ............... | 428/690 |
| 6,285,039 B1 * | 9/2001 | Kobori et al. ................ | 257/40 |

FOREIGN PATENT DOCUMENTS

| | | | |
|---|---|---|---|
| EP | 0892589 A1 | | 1/1999 |
| EP | 1 052 261 A1 | * | 11/2000 |
| WO | WO 97/29154 | | 8/1997 |
| WO | WO 0980836 A1 | | 2/1998 |
| WO | WO 99/40086 | * | 8/1999 |

OTHER PUBLICATIONS

*Nonlinear Optical Chromophores with Large Hyperpolarizabilities and Enhanced Thermal Stabilities*; Christopher R. Moylan, et al.; Reprinted from the Journal of the American Chemical Society; pp. 12599–12600; (1993). (no month).

*Organic Multicolor EL Display with Fine Pixels*; C. Hosokawa, et al.; Journal of the SID; pp. 331–334; (1997). (no month).

* cited by examiner

*Primary Examiner*—Marie Yamnitzky
(74) *Attorney, Agent, or Firm*—Connolly,Bove,Lodge & Hutz,LLP

(57) ABSTRACT

An organic light emitting display is provided which comprises as an emitting layer a fluorescent dye having at least one amine moiety substituted with two aryl groups. Also provided are new fluorescent compounds having N-aryl substituents which exhibit reduced pH sensitivity and enhanced stability to protonation.

4 Claims, No Drawings

ORGANIC LIGHT EMITTING DISPLAYS AND NEW FLUORESCENT COMPOUNDS

TECHNICAL FIELD

The present invention relates to organic light emitting displays (OLED) and more particularly to organic light emitting displays comprising fluorescent dyes having an amine moiety substituted with two aryl groups in the emitting layer. Organic light emitting displays of the present invention exhibit increased fluorescent efficiency.

The present invention also relates to new fluorescent compounds having amine moiety substituted with two aryl groups which are useful in the organic light emitting displays, as well as for other purposes such as laser dyes, fluorescent probes in biological systems and in electro-optical applications.

BACKGROUND OF INVENTION

An electric display device is an electronic device for visually transmitting information from a machine to a person, thereby acting as an interface. Among the more promising emerging display technologies is the organic light emitting display (OLED).

One of the simpler routes to full-color organic light emitting diode (OLED) displays uses thin films containing fluorescent dyes to down-convert blue emitted light to green and red. These fluorescent materials need to have high absorbance in the blue wavelengths, high fluorescence efficiencies in the green or red wavelengths and be photo-oxidatively stable. These color-conversion materials must be patterned to match the size of the sub-pixels in the display.

At present, many of the known fluorescent materials have the correct color spectra but suffer from photo-degradation and low fluorescence quantum yields and furthermore are too basic to be incorporated into a directly patternable manufacturing process. Some fluorescent dyes have strongly pH-dependent absorption and fluorescence characteristics. This puts limits on the pH range of the medium in which the fluorophore is useful. This pH sensitivity is due to the reconfiguration of the fluorophores that occurs upon protonation. For example, current fluorophores containing dialkylamine groups are subject to protonation in the presence of acid.

One particular problem found with pH-sensitive fluorescent dyes is in their use in color-conversion materials. In the case of small pixels (2–50 microns in width) found in micro- and compact displays, the ability to use a photopatternable material as the matrix for the fluorescent dyes would be a very attractive patterning scheme. Unfortunately, the most commonly used fluorescent dyes contain primary or alkyl substituted amines as part of the chromophore. These pH-sensitive amines are incompatible with the chemistry of most modern photoresists, in particular the acid generated during exposure protonates the dialkylamine, bleaches the fluorescent dye, and renders the color-converter useless. Many current lithographic processes employ acid catalyzed chemically amplified photoresists. Accordingly, there exists a need to provide for improved fluorescent materials.

SUMMARY OF INVENTION

The present invention provides fluorescent materials which do not suffer from the above problems and disadvantages and consequently are more suitable for use in OLED systems. Fluorescent materials of the present invention exhibit enhanced fluorescence efficiency and photo-oxidative stability, and are relatively insensitive to pH.

Fluorescent materials used in the present invention, being relatively pH-insensitive, are capable of surviving photopatterning processes involving photo-acid generators. Accordingly, simpler direct routes to photolithographically patterned color-converters can be used.

It has surprisingly been found according to the present invention that amine fluorescent compounds having an amine moiety substituted with two aryl groups have much higher fluorescence efficiency than their alkyl substituted analogs, making the color-conversion films more efficient as well. Photo-oxidative stability is another unexpected feature of the compounds employed pursuant to the present invention.

Accordingly, the present invention relates to an organic light emitting display which comprises a hole transporting/anode layer, an electron transporting/cathode layer and an emitting layer located intermittent the anode layer and cathode layer. The emitting layer comprises a fluorescent dye having at least one amine moiety substituted with two aryl groups.

A further aspect of the present invention relates to fluorescent compounds selected from the group consisting of

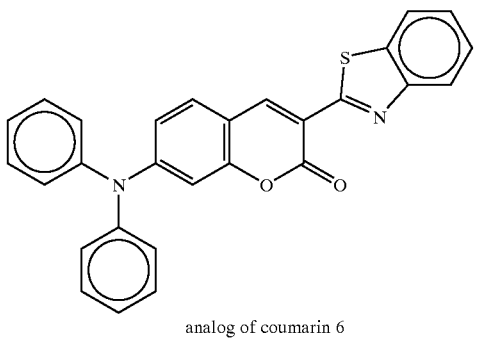

analog of coumarin 6

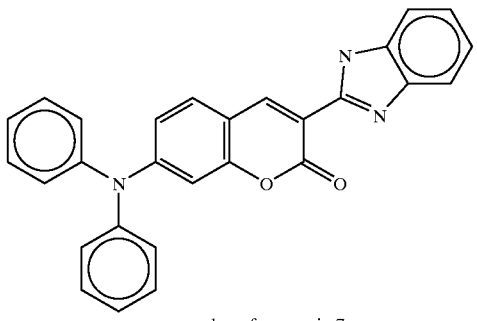

analog of coumarin 7

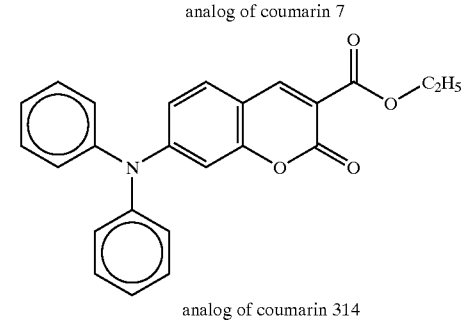

analog of coumarin 314

-continued

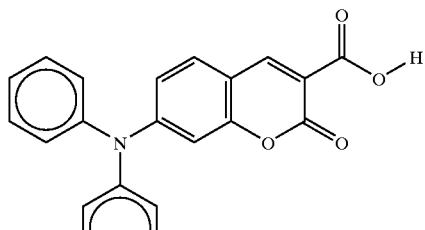

analog of coumarin 343

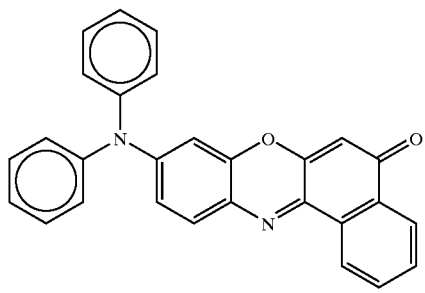

analog of Phenoxazone 9
and

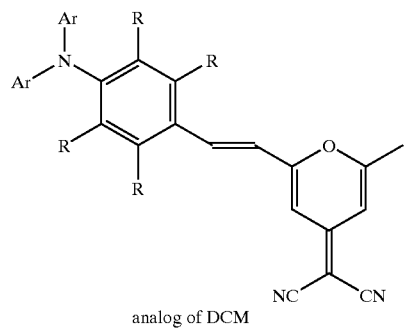

analog of DCM wherein each R individually is selected from the group consisting of H, alkyl, substituted alkyl, aryl, substituted aryl, halogen, carboxylic acid and derivatives thereof, hydroxy, alkoxy, aryloxy, nitro, sulfonic acid and derivatives; substituted and unsubstituted heterocyclic. The various R groups can be the same or different from each other.

Each Ar individually is an aryl or substituted aryl group.

A still further aspect of the present invention relates to compositions containing polymeric resist and a fluorescent dye having an amine moiety substituted with two aryl groups.

Still other objects and advantages of the present invention will become readily apparent by those skilled in the art from the following detailed description, wherein it is shown and described preferred embodiments of the invention, simply by way of illustration of the best mode contemplated of carrying out the invention. As will be realized the invention is capable of other and different embodiments, and its several details are capable of modifications in various obvious respects, without departing from the invention. Accordingly, the description is to be regarded as illustrative in nature and not as restrictive.

BEST AND VARIOUS MODES FOR CARRYING OUT INVENTION

The compounds employed according to the present invention are fluorescent dyes that have at least one amine moiety substituted with two aryl groups. The preferred aryl substituent is phenyl. Examples of other suitable aryl groups are naphthyl, anthracyl, dinaphthyl, ditoluyl, bis(p-methylphenyl), dianthracenyl, mixed aryl groups such as phenylnaphthyl and phenyltoluyl, and substituted aryl groups such as toluyl.

The fluorescent dyes can be used as an emitting layer in light emitting displays. Pixels of the fluorescent dyes can be fabricated by any of the well known techniques such as use of photoresists for photolithographic patterning, ink jet printing and evaporation through a shadow mask.

The organic light emitting displays further include a hole transporting/anode layer and an electron transporting/cathode layer. Materials for these layers are well known and need not be described herein. Examples of such can be found in U.S. Pat. Nos. 5,126,214, 5,294,870, 5,705,285 and EP 892 589 A1, disclosures of which are incorporated herein by reference.

Examples of some preferred compounds employed in the present invention are represented by the following formulae

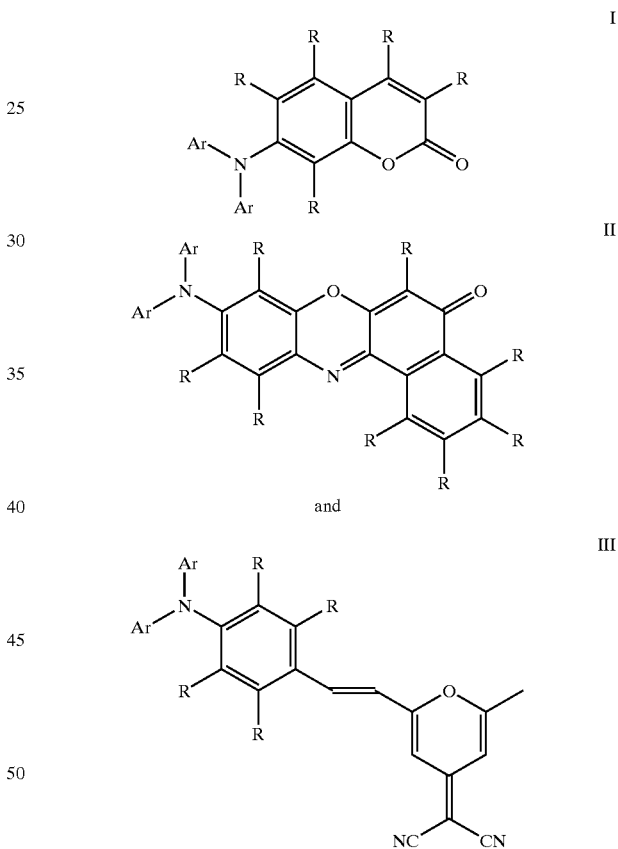

analog of DCM wherein each R individually is selected from the group consisting of H, alkyl, substituted alkyl, aryl, substituted aryl, cycloalkyl, halogen, carboxylic acid and derivatives thereof, hydroxy, alkoxy, aryloxy, nitro, sulfonic acid and derivatives thereof, substituted and unsubstituted heterocyclic; and each Ar individually is an aryl or substituted aryl.

Listed below are definitions of various terms used to describe this invention. These definitions apply to the terms as they are used throughout this specification, unless otherwise limited in specific instances, either individually or as part of a larger group.

The term "alkyl" refers to straight or branched chain unsubstituted hydrocarbon groups of 1 to 20 carbon atoms, preferably 1 to 8 carbon atoms, and more preferably unsubstituted alkyl groups of 1 to 4 carbon atoms.

The term "substituted alkyl" typically refers to an alkyl group substituted by, for example, one to four substituents, such as halo, trifluoromethyl, trifluoromethoxy, hydroxy, thiol, alkylsulfonyl, arylsulfonyl, aralkylsulfonyl, sulfonamido (e.g. $SO_2NH_2$), substituted sulfonamido, nitro, cyano, carboxy, carbamyl (e.g. $CONH_2$) substituted carbamyl (e.g. CONH alkyl, CONH aryl, CONH aralkyl or cases where there are two substituents on the nitrogen selected from alkyl, aryl or aralkyl). Where noted above where the substituent is further substituted it will be with halogen, alkyl, alkoxy, aryl or aralkyl.

The term "halogen" or "halo" refers to fluorine, chlorine, bromine and iodine.

The term "aryl" refers to monocyclic or polycyclic aromatic hydrocarbon groups having 6 to 18 carbon atoms in the ring portion, such as phenyl, naphthyl, diphenyl anthracenyl, dinaphthyl, ditoluyl, bis(p-methylphenyl), dianthracenyl, mixed aryl groups such as phenylnaphthyl and phenyltoluyl groups, each of which may be substituted such as toluyl.

The term "aralkyl" or "alkylaryl" refers to an aryl group bonded directly through an alkyl group, such as benzyl or phenethyl.

The term "substituted aryl" or "substituted alkylaryl" typically refers to an aryl group or alkylaryl group substituted by, for example, one to four substituents such as alkyl; substituted alkyl, halo, trifluoromethoxy, trifluoromethyl, hydroxy, thiol, ureido, nitro, cyano, carboxy, carboxyalkyl, carbamyl, alkoxycarbonyl, alkysulfonyl, sulfonamido, and the like. The substituent may be further substituted by halo, hydroxy, alkyl, alkoxy, aryl, substituted aryl, substituted alkyl or aralkyl. "Substituted benzyl" refers to a benzyl group substituted by, for example, any of the groups listed above for substituted aryl.

The term "cycloalkyl" refers to optionally substituted, saturated cyclic hydrocarbon ring systems, preferably containing 1 to 3 rings and 3 to 7 carbons per ring which may be further fused with an unsaturated $C_3$–$C_7$ carbocyclic ring. Exemplary groups include cyclopropyl, cyclobutyl, cyclopentyl, cyclohexyl, cycloheptyl, cyclooctyl, cyclodecyl, cyclododecyl and adamantyl. Exemplary substituents include one or more alkyl groups as described above, or one or more groups described above as alkyl substituents.

The terms "heterocycle", "heterocyclic" and "heterocyclo" refer to an optionally substituted, fully saturated or unsaturated, aromatic or nonaromatic cyclic group, for example, which is a 4 to 7 membered monocyclic, 7 to 11 membered bicyclic, or 10 to 15 membered tricyclic ring system, which has at least one heteroatom in at least one carbon atom-containing ring. Each ring of the heterocyclic group containing a heteroatom may have 1, 2 or 3 heteroatoms selected from nitrogen atoms, oxygen atoms and sulfur atoms, where the nitrogen and sulfur heteroatoms may also optionally be oxidized and the nitrogen heteroatoms may also optionally be quaternized. The heterocyclic group may be attached at any heteroatom or carbon atom.

Exemplary monocyclic heterocyclic groups include pyrrolidinyl, pyrrolyl, indolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolidinyl, 2-oxazepinyl, azepinyl, 4-piperidonyl, pyridyl, N-oxo-pyridyl, pyrazinyl, pyrimidinyl, pyridazinyl, tetrahydropyranyl, tetrahydrothiopyranyl, tetrahydrothiopyranyl sulfone, morpholinyl, thiomorpholinyl, thiomorpholinyl sulfoxide, thiomorpholinyl sulfone, 1,3-dixolane and tetrahydro-1,1-dioxothienyl, dioxanyl, isothiazolidinyl, thietanyl, thiiranyl, triazinyl, and triazolyl, and the like.

Exemplary bicyclic heterocyclic groups include benzothiazolyl, benzoxazolyl, benzothienyl, quinuclidinyl, quinolinyl, quinolinyl-N-oxide, tetrahydroisoquinolinyl, isoquinolinyl, benzimidazolyl, benzopyranyl, indolizinyl, benzofuryl, chromonyl, coumarinyl, cinnolinyl, quinoxalinyl, indazolyl, pyrrolopridyl, furopyridinyl (such as furo[2,3-c]pyridinyl, furo[3,1-b]pyridinyl, or furo[2,3-b] pyridinyl), dihydroisoindolyl, diyhydroquinazolinyl (such as 3,4-dihydro-4-oxo-quinazolinyl), benzisothiazolyl, benzisoxazolyl, benzodiazinyl, benzofurazanyl, benzothiopyranyl, benzothrazolyl, benzpyrazolyl, dihydrobenzofuryl, dihydrobenzothienyl, dihydrobenzothiopyranyl, dihydrobenzothiopyranyl sulfone, dihydrobenzopyranyl, indolinyl, isochromanyl, isoindolinyl, naphthyridinyl, phthalazinyl, piperonyl, purinyl, pyridopyridyl, quinazolinyl, tetrahydroquinolinyl, thienofuryl, thienopyridyl, thienothienyl, and the like.

Exemplary substituents include one or more alkyl groups as described above or one or more groups described above as alkyl substituents.

The term "heteroatoms" shall include oxygen, sulfur and nitrogen.

Within the above-described definitions, certain embodiments are preferred. Preferred alkyl groups are lower alkyl groups containing 1 to about 8 carbon, and more preferably 1 to about 4 carbon atoms, and can be straight, branched-chain or cyclic saturated aliphatic hydrocarbon groups.

Examples of suitable alkyl groups include methyl, ethyl and propyl. Examples of branched alkyl groups include isopropyl and t-butyl. An example of a suitable alkylaryl group is phenethyl. Examples of suitable cycloalkyl groups typically contain 3–8 carbon atoms and include cyclopropyl, cyclobutyl, cyclopentyl and cyclohexyl. The aromatic or aryl groups are preferably phenyl or alkyl substituted aromatic groups (aralkyl) such as phenyl $C_{1-3}$ alkyl such as benzyl.

The N-heterocyclic rings preferably contain 3–7 atoms in the ring and a heteroatom such as N, S or O in the ring. Examples of suitable preferred heterocyclic groups are pyrrolidino, azetidino, piperidino, 3,4-didehydropiperidino, 2-methylpiperidino and 2-ethylpiperidino. In addition, the above substitutions can include halo such as F, Cl, Br, lower alkyl, lower alkoxy and halo substituted lower alkoxy.

The carboxylic acids typically contain 1–12 carbon atoms and more typically 1–4 carbon atoms. Examples of suitable derivatives of carboxylic acids include esters, amides and nitrile derivatives. The ester and amide derivatives typically contain 1–12 carbon atoms and more typically 1–4 carbon atoms.

The alkoxy and aryloxy groups typically contain 1–20 carbon atoms, more typically 1–8 carbon atoms and preferably 1–4 carbon atoms.

Examples of the sulfonic acid derivatives are sulfonates and esters, which typically contain 1–12 carbon atoms and more typically 1–4 carbon atoms.

Examples of some particularly preferred novel compounds of the present invention in formulae I,II and III are diphenyl analogs of:

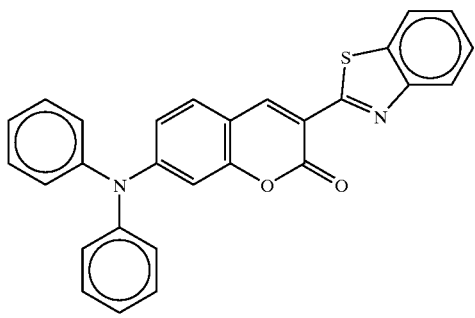

analog of coumarin 6

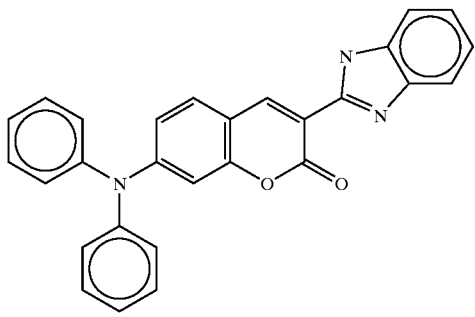

analog of coumarin 7

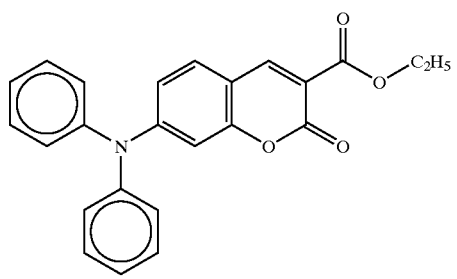

analog of coumarin 314

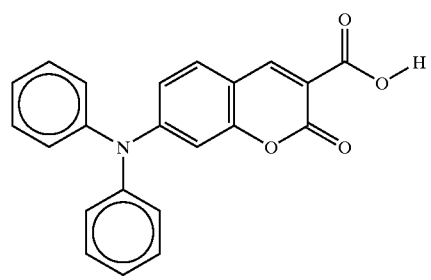

analog of coumarin 343

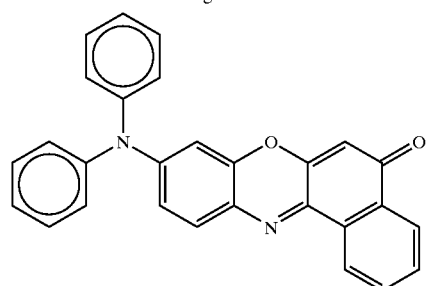

analog of Phenoxazone 9 and

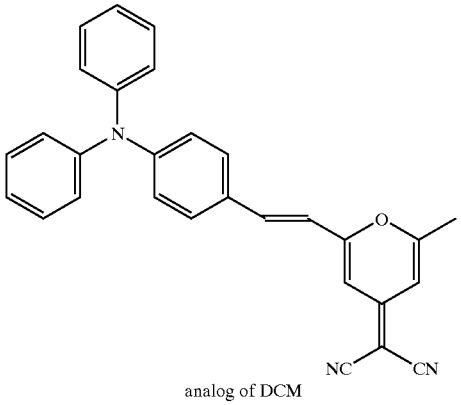

analog of DCM

Compositions employing the fluorescent dyes according to the present invention typically include about 1% to about 50% by weight and more typically about 5% to about 25% by weight of a resist polymer and about 0.1% to about 5% by weight of the dye and more typically about 0.5% to about 1% by weight of the dye, and the remainder of the composition can be substantially an organic solvent.

Typical resist polymers include epoxy resins such as SU-8, acrylate resins, methacrylate resins, styrene resins and the like. The compositions may also include sensitizers, initiators, photoacid generators, and the like.

The following non-limiting examples are presented to further illustrate the present invention.

EXAMPLE 1

Preparation of the Diphenyl Analog of Courmain 314

Step 1

3-methoxytriphenylamine was prepared by a phase transfer variant of the Ullmann coupling procedure (S. Gauthier and J. M. J. Fréchet, Synthesis, 1987, 1331) in which 37.34 g m-Anisidine, 142.47 g iodobenzene, 74.93 g copper powder, 2.20 g 18-crown-6 and 320.8 g anhydrous potassium carbonate in 500 ml phenyl ether were placed into a 1 liter three necked round bottom flask equipped with overhead stirrer, reflux condenser, nitrogen inlet, thermowell, and heating mantle and heated at reflux overnight. The solids were removed by filtration and the solvents by vacuum distillation. The resulting brown oil is used in step 2 below.

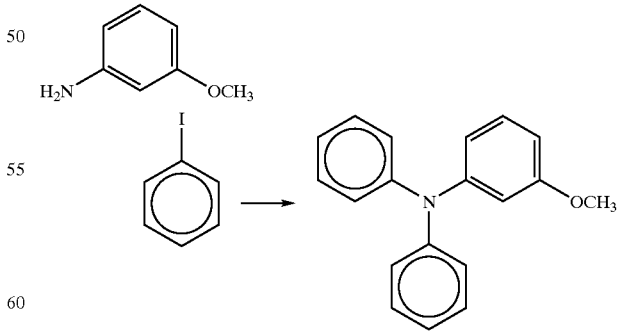

Step 2

3-hydroxytriphenylamine was prepared by cleaving the methoxy ether using freshly prepared aluminum iodide. 9.92 g aluminum, 140 g iodine and 200 ml acetonitrile were placed in a 3 necked 500 ml round bottom flask equipped with magnetic stirring, a reflux condenser, nitrogen inlet and an additionl funnel containing the 3-methoxytriphenylamine from step 1 dissolved in 100 ml acetonitrile. The mixture of aluminum, iodine and acetonitrile was refluxed with stirring until the purple color of the iodine disappeared. The solution of 3-methoxytriphenylamine was then added and the resulting mixture was refluxed overnight. After cooling, the reaction mixture was poured onto ice and extracted into ether. The etherate phase was washed with sodium hydrosulfite, dried over magnesium sulfate, filtered, rotary evaporated to remove solvent and dried in a vacuum oven. The oil is used in step 3 below.

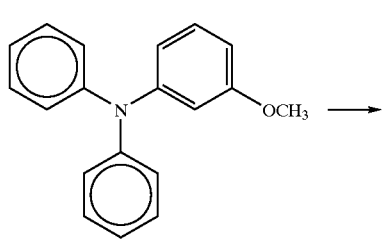

Step 3

The diphenyl analog of coumarin 314 was prepared by the condensation (E. R. Bissell, Synthesis, 1982, 846–848) of 3-hydroxytriphenylamine with diethyl ethoxymethylenemalonate. 73.86 g of 3-hydroxytriphenylamine from step 2, 69.95 g diethylethoxymethylenemalonate and 200 ml THF were placed in a 113 necked round bottom flask equipped with reflux condenser, heating mantle, magnetic stirrer and a flexible tube connected to a 100 ml round bottom flask containing 43 ml titanium (IV) chloride which was added quickly but slow enough to prevent overheating. The mixture was allowed to reflux overnight. The cooled mixture was poured into 3l water containing 18 ml concentrated hydrochloride acid. The coumarin was extracted into methylene chloride and washed with water, 1 N sodium hydroxide, and water, dried over magnesium sulfate, filtered and rotary evaporated to remove solvent. The coumarin was purified by flash chromatography in methylene chloride.

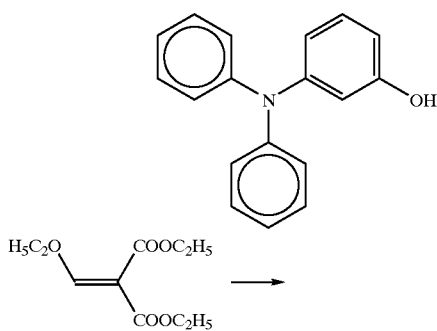

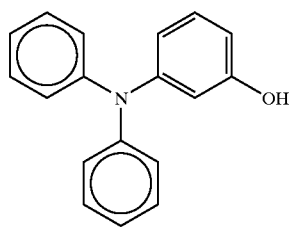

-continued

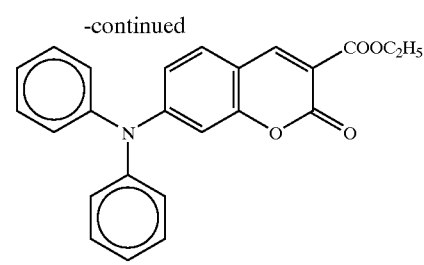

EXAMPLE 2

The diphenyl analog of coumarin 343 was prepared by the hydrolysis of the diphenyl analog of coumarin 314. 30 g of the diphenyl analog of coumarin 343 prepared according to Example 1 was dissolved in 200 ml methanol in a 500 ml round bottomed flask equipped with a reflux condenser, magnetic stirrer and heating mantle. The solution was taken to reflux, 187 ml of 0.5 N NaOH solution was added, the mixture was taken to reflux again, and then allowed to cool to room temperature. 2N HCl was added to acidify the solution and the organics were extracted into ether, washed with 2N HCl and water, transferred to a 500 ml round bottom flask and rotary evaporated to remove solvent. 500 ml methanol was added and the solid was triturated overnight. The solid product was filtered and dried under vacuum.

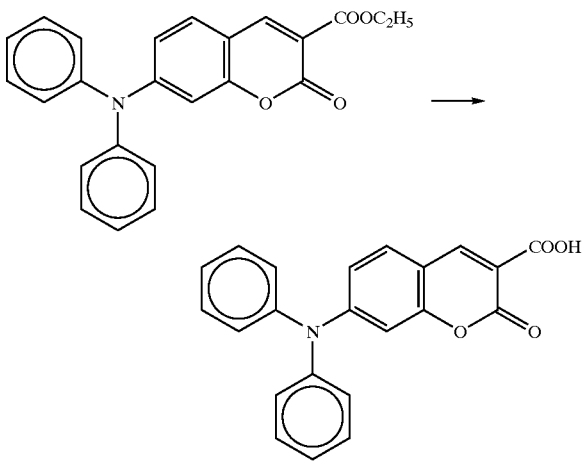

EXAMPLE 3

The diphenyl analog of coumarin 6 was prepared by the thermal condensation of 2-aminothiophenol with the diphenyl analog of coumarin 314. 7.5 g of the diphenyl analog of coumarin 314 prepared according to Example 1, 2.45 g of 2-aminothiophenol, 15 g diphenyl, and 15 g phenyl ether were placed in a 50 ml round bottom flask and taken to reflux for 30 minutes. After cooling to room temperature, 50 ml of toluene was added and the product was isolated by filtration, washed with ether, dried in vacuum, and recrystallized from methylene chloride/ethyl acetate.

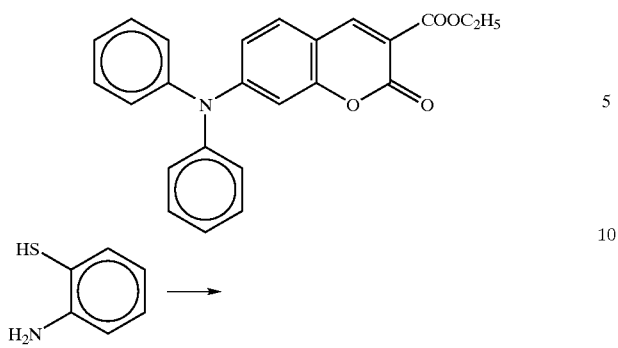

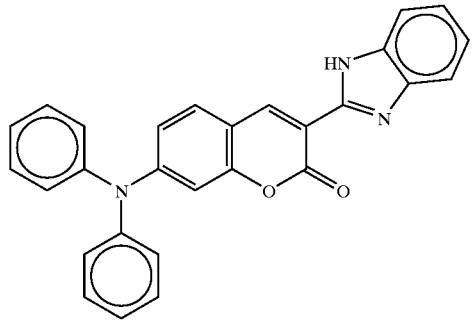

EXAMPLE 5

The diphenyl analog of DCM was prepared (e.g. general procedure, in Bourson et al, J. Phys. Chem. 1989, 93, 3871–3876) by the reaction of 17.22 g 4-dicyanomethylene-2,6-dimethyl-4-H-pyran with 27.33 g p-diphenylaminobenzaldehyde in 250 ml 1-propanol with 8.51 g piperidine. After refluxing overnight, the reaction was cooled and the dimer, DADP, precipitated. The filtrate was rotary evaporated to remove the solvents and recrystallized from methylene chloride/ethyl acetate/hexane.

EXAMPLE 4

The diphenyl analog of coumarin 7 was prepared by the dehydration/condensation (J. B. Hendrickson, M. S. Hussoin, J. Org. Chem. 1987, 52, 4139–4140) of o-phenylenediamine with the diphenyl analog of coumarin 343. A solution of 7.9 ml of triflic anhydride in 150 ml methylene chloride was added to a solution of 26.16 g triphenylphosphine oxide in 150 ml methylene chloride at 0° C. under nitrogen atmosphere. The resulting mixture was allowed to come to room temperature and a solution of 2.54 g o-phenylenediamine and 7 g diphenyl analog of coumarin 343 prepared according to the method of Example 2 in 80 ml methylene chloride was added dropwise. The slurry was stirred overnight. The reaction mixture was washed with 5% sodium bicarbonate, water and brine, dried of magnesium sulfate, filtered, and rotary evaporated to remove the solvent. The product was isolated by flash column chromatography in methylene chloride.

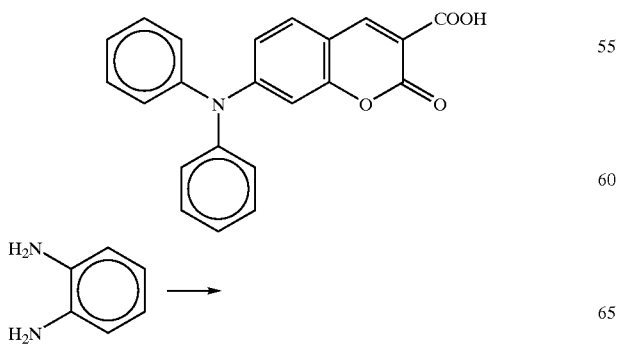

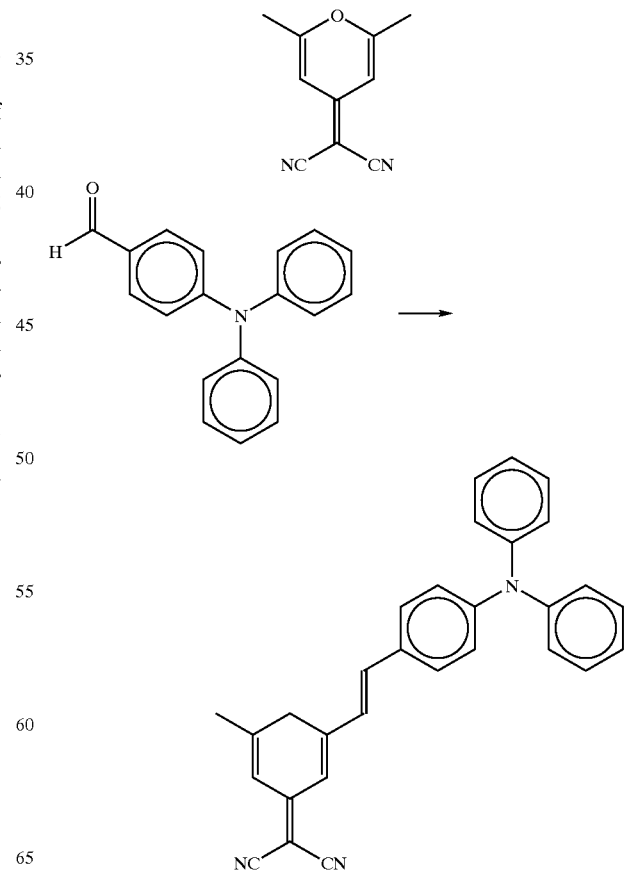

EXAMPLE 6

Step 1

5-diphenylamino-2-nitrosophenol hydrochloride is prepared by dissolving 44.3 g of 3-hydroxytriphenylamine (from Example 1, Steps 1–2) in 100 ml acetonitrile containing 100 ml concentrated hydrochloric acid and 60 ml water, cooling to –5° C. using an ice bath, and adding a solution of 15.0 g sodium nitrite in 100 ml 1:1 water/brine slowly below the surface of the solution followed by another 50 ml brine. The reaction is stirred in the ice bath for 1 hour and then water is added to precipitate the product which was filtered and used directly in the next step.

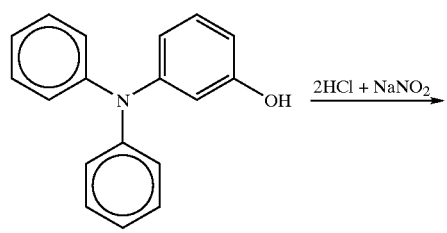

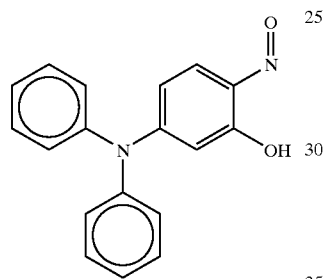

Step 2

The 5-diphenylamino-2-nitrosophenol hydrochloride and 30 g 1-naphthol was dissolved in 500 ml dimethylformamide and taken to reflux for 3 hours. After cooling to room temperature, the reaction mixture was poured into water and 5% ammonium hydroxide solution was added to neutralize the solution. The precipitate was filtered, washed with water and dried in a vacuum oven. The diphenyl analog of Phenoxazone 9 was purified by flash chromatography on silica gel using methylene chloride as the eluent, followed by recrystallization from chloroform.

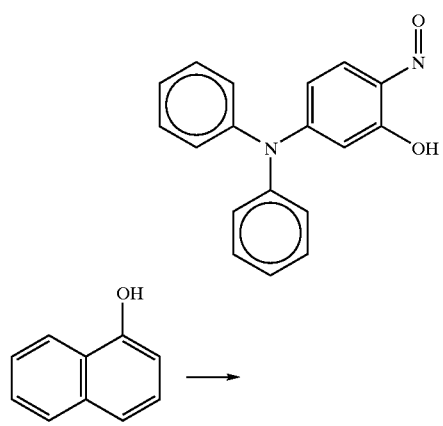

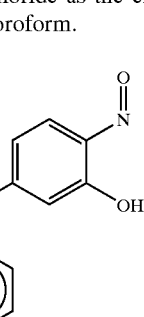

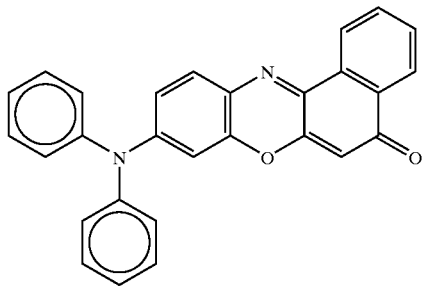

EXAMPLE 7

Polymer films of polymethylmethacrylate (PMMA) containing about 5% of the diaryl analog of coumarin 6 were fabricated and the fluorescence was measured. The films fluorescence efficiency was 80%.

Comparison Example 7

Example 7 was repeated except that the dye used was coumarin 6. These films had a fluorescence efficiency of only 30%. The enhancement in fluorescence efficiency according to this invention translates directly into a power savings for the display.

EXAMPLE 8

The diaryl analog of coumarin 6 was exposed to air and light for a two week period and tested for fluorescence. The diaryl analog lost less than 5% of its fluorescence.

Comparison Example 8

Example 8 was repeated except that coumarin 6 was used. Coumarin 6 lost about ⅓ of its fluorescence. These results evidence the enhancement of the photo-oxidative stability of the compounds of the present invention.

EXAMPLE 9

Films of an epoxy resin (SU-8) containing 5% of the diarylamine analog of coumarin 314, 5% TBIT (a photo acid generator), and 5% 9-anthracenemethanol (sensitizer) were prepared and exposed to 540 mJ at 365 nm. The resulting crosslinked film showed no bleaching. This makes it possible to use modern photo-lithographic techniques for manufacturing the full-color OLED.

The foregoing description of the invention illustrates and describes the present invention. Additionally, the disclosure shows and describes only the preferred embodiments of the invention but, as mentioned above, it is to be understood that the invention is capable of use in various other combinations, modifications, and environments and is capable of changes or modifications within the scope of the inventive concept as expressed herein, commensurate with the above teachings and/or the skill or knowledge of the relevant art. The embodiments described hereinabove are further intended to explain best modes known of practicing the invention and to enable others skilled in the art to utilize the invention in such, or other, embodiments and with the various modifications required by the particular applications or uses of the invention. Accordingly, the description is not intended to limit the invention to the form disclosed herein. Also, it is intended that the appended claims be construed to include alternative embodiments.

What is claimed is:
1. A fluorescent compound with the structural formula
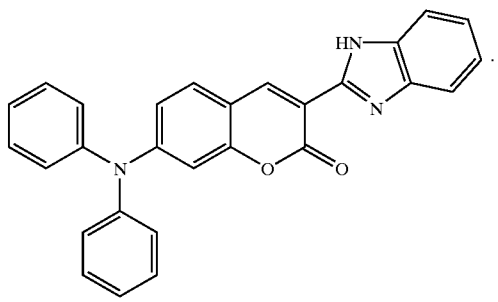
2. An organic light emitting display with a fluorescent compound having the structural formula
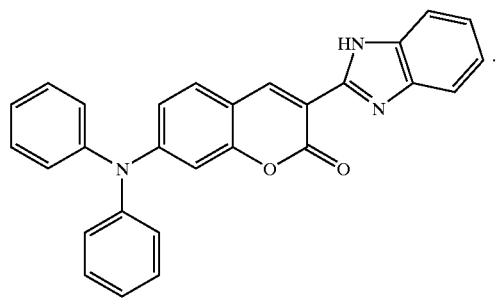
3. A photoresist composition comprising an epoxy resin and a coumarin 7 analog of formula
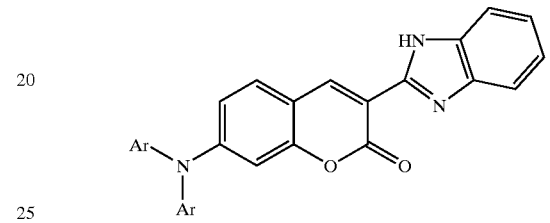
wherein Ar is aryl or substituted aryl.
4. The composition of claim 3 wherein Ar is phenyl.
* * * * *